US012023271B2

United States Patent
Yeung

(10) Patent No.: US 12,023,271 B2
(45) Date of Patent: Jul. 2, 2024

(54) UNOBTRUSIVE ELBOW BRACE

(71) Applicant: PRIMEDTECH LIMITED, Central (HK)

(72) Inventor: David K Yeung, Hong Kong (HK)

(73) Assignee: Primedtech Limited, Central (HK)

( * ) Notice: Subject to any disclaimer, the term of this patent is extended or adjusted under 35 U.S.C. 154(b) by 911 days.

(21) Appl. No.: 17/047,007

(22) PCT Filed: Mar. 29, 2019

(86) PCT No.: PCT/CN2019/080418
§ 371 (c)(1),
(2) Date: Oct. 12, 2020

(87) PCT Pub. No.: WO2019/196682
PCT Pub. Date: Oct. 17, 2019

(65) Prior Publication Data
US 2021/0069004 A1    Mar. 11, 2021

Related U.S. Application Data

(60) Provisional application No. 62/657,029, filed on Apr. 13, 2018.

(51) Int. Cl.
*A61F 5/37* (2006.01)
*A45C 3/06* (2006.01)
(Continued)

(52) U.S. Cl.
CPC .............. *A61F 5/3738* (2013.01); *A45C 3/06* (2013.01); *A45C 9/00* (2013.01); *A45C 13/103* (2013.01);
(Continued)

(58) Field of Classification Search
CPC ........ A61F 5/3738; A61F 5/37; A61F 5/3715; A61F 5/3723; A61F 5/373; A45F 3/02;
(Continued)

(56) References Cited

U.S. PATENT DOCUMENTS 2,799,316 A * 7/1957 Cohen ...................... A45C 3/06
150/101
2,904,091 A * 9/1959 Reed ........................ A45C 3/06
150/117
(Continued)

FOREIGN PATENT DOCUMENTS

| CN | 201790133 U | * | 4/2011 |
| CN | 201790133 U |  | 4/2011 |
| WO | WO 2006124587 A2 |  | 11/2006 |

OTHER PUBLICATIONS

CN 201790133 U—Machine Translation—Espacenet (Year: 2023).*

*Primary Examiner* — Keri J Nelson
(74) *Attorney, Agent, or Firm* — Renner, Kenner, Greive, Bobak, Taylor & Weber

(57) ABSTRACT

An elbow brace for supporting a wearer's elbow in a desired position when using a portable electronic device to mitigate "tech neck" is made unobtrusive by incorporation into a shoulder bag having a length-adjustable shoulder strap. A flexible bag assembly comprises opposite first and second panels of flexible sheet-like material connected to define an interior compartment having a volume. An upper bag mouth is disposed between edges of the panels, with fastenings connecting its opposite ends of the edges. An elbow-receiving sleeve of flexible sheet-like material is attached in the upper bag mouth and can be opened into a generally frustoconical form, for supporting a bent elbow such that, in use, both forearm and upper arm extend from an outer end elbow-receiving sleeve. In a closed state the elbow-receiving sleeve is flattened such that opposing halves of the elbow-receiving sleeve come together.

12 Claims, 4 Drawing Sheets

(51) Int. Cl.
*A45C 9/00* (2006.01)
*A45C 13/10* (2006.01)
*A45F 3/02* (2006.01)

(52) U.S. Cl.
CPC ........ *A45F 3/02* (2013.01); *A45C 2013/1015* (2013.01)

(58) Field of Classification Search
CPC .... A45C 3/00; A45C 3/06; A45C 9/00; A45C 13/103; A45C 1/00; A45C 1/02; A45C 1/024; A45C 2013/1015
See application file for complete search history.

(56) References Cited

U.S. PATENT DOCUMENTS

| | | | | |
|---|---|---|---|---|
| 3,708,005 | A * | 1/1973 | Crain | A45C 3/00 190/126 |
| 3,938,569 | A * | 2/1976 | Hill | A45C 3/06 5/653 |
| 5,489,021 | A * | 2/1996 | Wallingford | B42F 13/40 206/214 |
| 5,816,460 | A * | 10/1998 | Cook | A45F 3/14 224/604 |
| 6,336,576 | B1 | 1/2002 | Easter | |
| 2002/0134896 | A1 | 9/2002 | Hunter | |
| 2013/0062375 | A1 | 3/2013 | Finch | |
| 2014/0326371 | A1 * | 11/2014 | Lewis | A45C 7/0068 150/117 |
| 2017/0056232 | A1 * | 3/2017 | Yeung | A61F 5/0118 |
| 2018/0228637 | A1 * | 8/2018 | Elzik | A61F 5/3738 |
| 2021/0113360 | A1 * | 4/2021 | Paul | A61F 5/3715 |

* cited by examiner

UNOBTRUSIVE ELBOW BRACE

TECHNICAL FIELD

The present invention relates to elbow braces, more particularly to an unobtrusive elbow brace for supporting a wearer's elbow in a desired position during the use of portable electronic devices to encourage a posture that mitigates "tech neck".

BACKGROUND OF THE INVENTION

With the increased use of portable electronic devices has come an increase in reports of "tech neck"—neck pain and upper back pain and injury, believed to be related to the tendency for these devices to be used for long stretches of time in a head-forward posture. Supporting the head in this cantilevered manner places strain upon the neck, and this is a key area of concern. To a lesser degree, constantly outstretching the arm to support the device can also be a cause of wrist pain and injury. Even when injury does not result, the prolonged and continuous use of such portable electronic devices can cause fatigue and other temporary discomfort. A need therefore exists for a solution which relieves the neck, shoulders, back, elbows and wrists from the effects of improper loading, such as that which occurs when operating a portable electronic device.

Typical prior art solutions to this problem provide a device holder that supports the device at or near eye level. They may comprise a harness, such as a neck ring, or a back frame carried by shoulder straps, from which cantilever structure projects, with the device holder mounted at one end. However, these solutions have the drawbacks of being cumbersome and obtrusive, their size and weight makes them difficult to store and carry around, and their relative complexity makes them costly, and time-consuming to set up for use.

Arm slings are employed for supporting the forearm of a patient and comprise a pouch that is supported by a strap around the patient's shoulder. The patient's forearm rests within the pouch such that the elbow is at a 90° angle and the forearm extends across his abdomen. Current arm slings, including those described above, function to restrict the normal manipulation of an injured arm and do not support a patient's forearm upright, or with any upright component. As such, they provide ergonomically unsatisfactory positioning of any device held in the patient's hand.

US2013/0062375 describes sling-type product in which opposite ends of an elongate carrier are fixed to the ends of a shoulder strap. The carrier has a surface for supporting the forearm horizontally along one side of the abdomen, and an elbow cup at one of the ends. An advantage of this sling-type arm support is the versatility it offers for carrying different loads in shopping bags having handles, as a row of hooks are provided on the carrier, from which the handles can be hung. However, this product otherwise generally suffers from the above-mentioned drawbacks of both device holders and arm slings.

It is an object of the present invention to overcome or substantially ameliorate the above disadvantages or, more generally, to provide an improved unobtrusive elbow brace.

DISCLOSURE OF THE INVENTION

According to one aspect of the present invention there is provided an unobtrusive elbow brace comprising:

a length-adjustable shoulder strap assembly having longitudinally opposing ends;

a flexible bag assembly comprising: opposite first and second panels of flexible sheet-like material that are mutually connected to define an interior compartment, upper edges of the first and second panels being mutually connected at opposite ends to form an upper bag mouth therebetween, a fastening at each of the opposite ends, the fastenings connecting respective ones of the opposing ends of the length-adjustable strap assembly;

an elbow-receiving sleeve formed of flexible sheet-like material and attached in the upper bag mouth for movement between open and closed states, the elbow-receiving sleeve tapering to narrow from an outer end proximate the upper edges, to an inner end, in the open state the elbow-receiving sleeve having with a generally frustoconical form, with an included cone angle between 75° and 105°, wherein, in use, the elbow-receiving sleeve receives a wearer's bent elbow such that both forearm and upper arm extend from the outer end, and in the closed state the elbow-receiving sleeve is flattened such that opposing halves of the elbow-receiving sleeve come together.

Preferably the frustoconical form has a central axis, and the fastenings are disposed along a transverse axis substantially equidistant either side of the central axis.

Preferably the flexible sheet-like material of the elbow-receiving sleeve comprises an elastomer. Preferably the elastomer comprises a foamed elastomer sheet. Preferably the foamed elastomer sheet is laminated to at least one textile piece.

Preferably the flexible sheet-like material of the first and second panels comprises a textile.

The flexible bag assembly may further comprise first and second lining sheets between the first and second panels for forming a lining of the interior compartment.

In one embodiment each half of the elbow-receiving sleeve is fixed generally at or adjacent both the inner and outer ends to one of the first and second panels, as by stitching or adhesive. Alternatively, each half of the elbow-receiving sleeve may be fixed only at or adjacent the outer end to one of the first and second panels, such that the inner end of the elbow-receiving sleeve hangs from the outer end in use, free of the first and second panels. The elbow-receiving sleeve may further comprise an end piece of flexible-sheet material that closes the inner end and, in this configuration, the elbow-receiving sleeve may close the upper bag mouth.

The halves of the elbow-receiving sleeve may be joined by at least one seam. The at least one seam may be positioned such that when the elbow-receiving sleeve is flattened it folds along the at least one seam.

Preferably the flexible bag assembly further comprises a closure for closing an access opening in one of the first and second panels for accessing the interior compartment. Preferably the closure is a zipper.

Preferably the shoulder strap assembly comprises an elongate strap, a tension-locked buckle connected to slide along the strap and with one end of the strap fixed thereto to form a first loop passing through the aperture in one of the fastenings, and a first coupler fixed at an intermediate position along the strap, an opposite end of the strap fixed to a second coupler complementary to the first coupler and passing through the aperture of the other of the fastenings to form a second loop when the first and second couplers are connected.

Preferably the first coupler is an eye and the second coupler is a hook with a mouth sized to receive the eye and closed by a resiliently mounted gate. However, it will be understood that any number of prior art couplers would be suitable alternatives in this application, such a plug and socket fasteners, snap domes, Velcro hook and eye fasteners etc.

Preferably the second coupler is unable to pass through the aperture of the other of the fastenings. Instead, another coupler like the first coupler may be fixed to the strap spaced apart from the intermediate position.

The invention provides an elbow brace that is readily used when sitting, standing or walking to maintain a head-up posture during use of a portable electronic device, and so mitigates neck and back pain which can otherwise occur. By incorporating the elbow brace into a commonly worn everyday item in an unobtrusive manner dual-purpose benefits can be obtained with a product that is more accessible to users of portable electronic devices.

BRIEF DESCRIPTION OF THE DRAWINGS

Preferred forms of the present invention will now be described by way of example with reference to the accompanying drawings, wherein.

DESCRIPTION OF THE PREFERRED EMBODIMENTS

Figure 1:
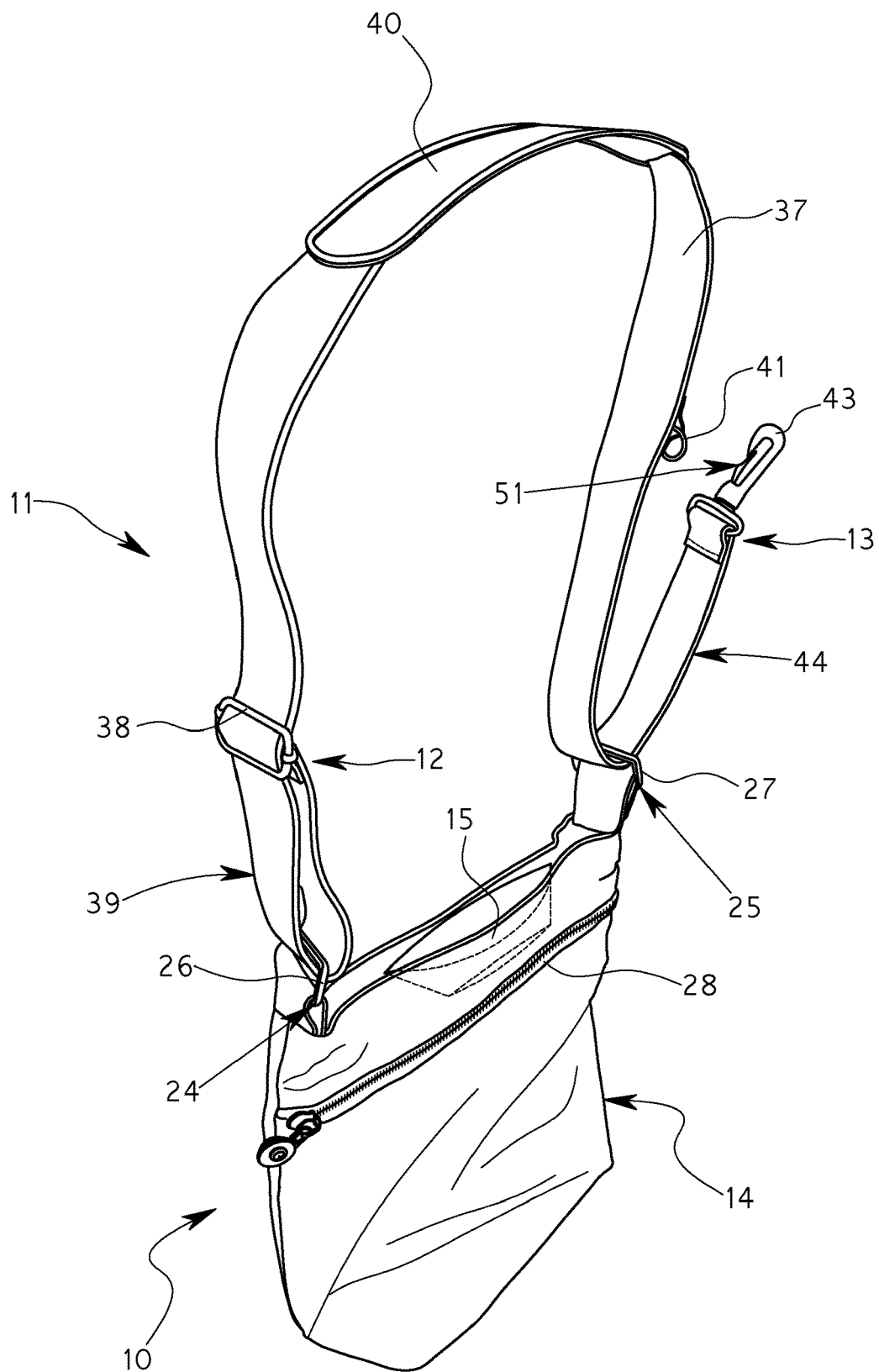
FIG. 1 is a perspective view of an unobtrusive elbow brace of the invention.
Figure 2:
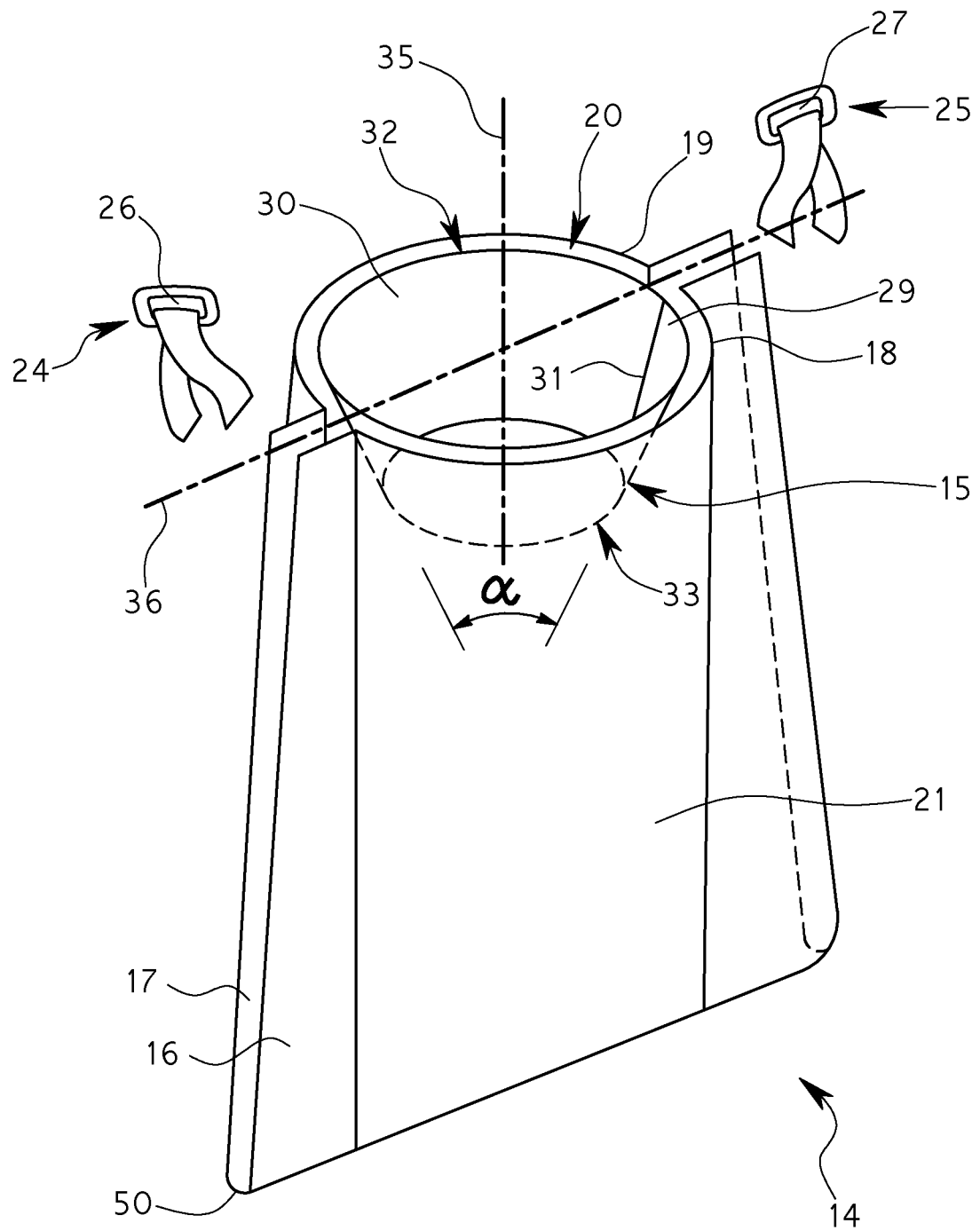
FIG. 2 is a schematic perspective view of a bag assembly and elbow-receiving sleeve of the unobtrusive elbow brace of FIG. 1 with the elbow-receiving sleeve in an open state.
Figure 3:
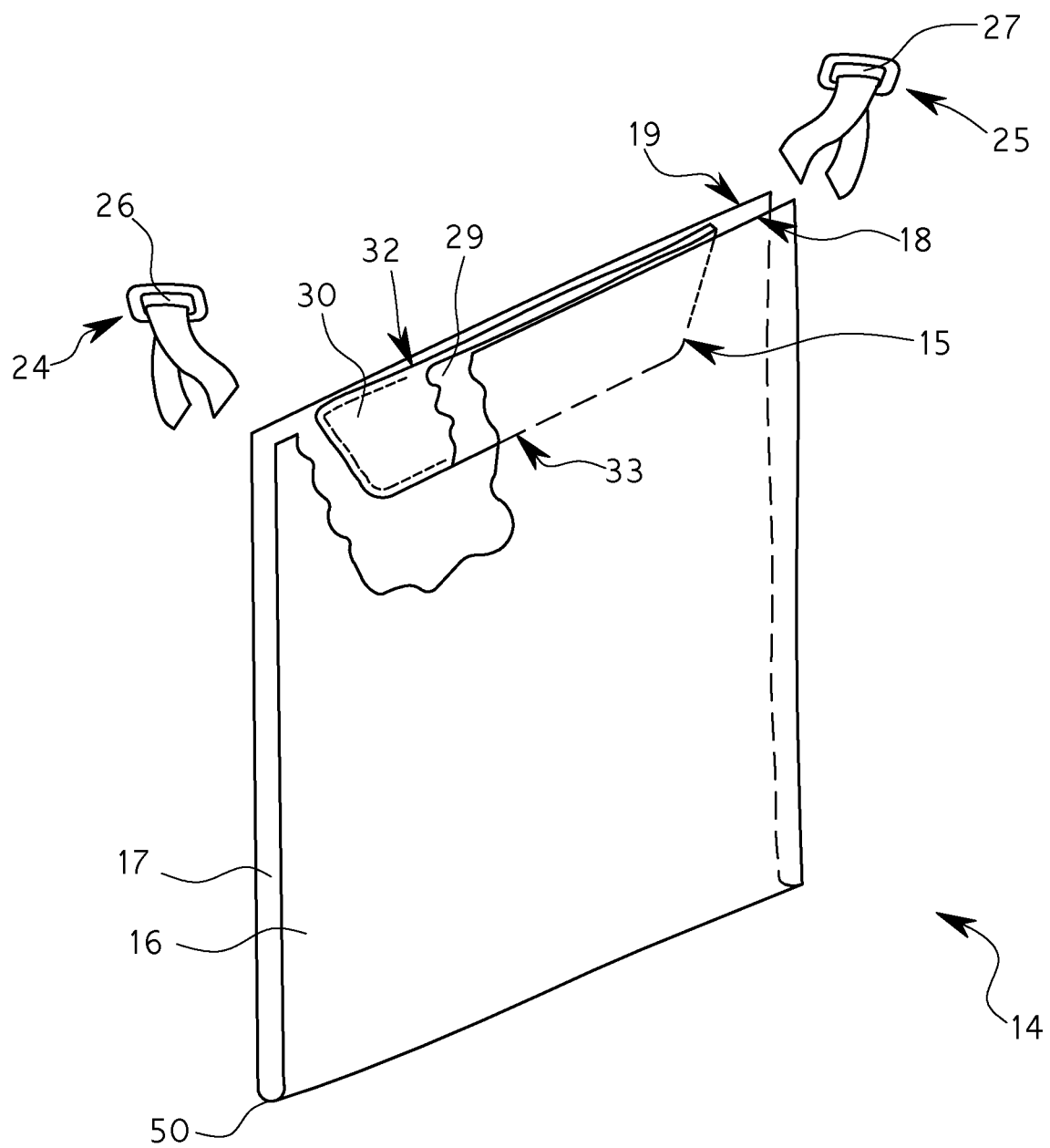
FIG. 3 is a schematic perspective view of the bag assembly and elbow-receiving sleeve of FIG. 2 with the elbow-receiving sleeve in closed state.

Referring to FIGS. 1 to 3, an elbow brace for supporting a wearer's elbow in a desired position when holding a portable electronic device is made unobtrusive by incorporation into a shoulder bag. The unobtrusive elbow brace 10 of the invention may also be considered a combination shoulder bag and elbow brace. The unobtrusive elbow brace 10 includes a length-adjustable shoulder strap assembly 11 having two longitudinally opposing ends 12, 13 connectable to a flexible bag assembly 14 that supports an elbow-receiving sleeve 15 for receiving an elbow of a user.

The flexible bag assembly 14 includes at least opposing first and second panels 16, 17 which may be made of a textile, or other flexible sheet-like material. The panels 16, 17 may both be of like form and generally rectangular. The panels 16, 17 may be mutually connected, along part of their perimeters, as by a fold (for instance, fold 50 along the lower edge) and seams (not shown) along opposite long edges, to form a bag with an upper bag mouth 20 between the panels 16, 17. In addition to folds and stitched seams, the panels 16, 17 may be mutually connected along part of their perimeters by adhesive, and/or by additional panels (not shown). In this manner the panels 16, 17 for a bag and define therebetween an interior compartment 21 having a volume for storing personal items etc. Uppermost edges 18, 19 of the first and second panels 16, 17 are mutually connected only at opposite ends i.e. at either side of the upper bag mouth 20. The upper bag mouth 20 is sized to receive the elbow-receiving sleeve 15.

The bag assembly 14 further includes a fastening 24, 25 at each of the opposite ends of the upper bag mouth 20 with each of the fastenings 24, 25 having an aperture 26, 27. The fastenings 24, 25 serve for connecting respective ones of the opposing ends 12, 13 of the shoulder strap assembly 11. In this manner the bag assembly 14 effectively hangs between these two fastenings 24, 25 in use. The fastenings 24, 25 are disposed along a transverse axis 36 generally equidistant from either side of the central axis 35. The fastenings 24, 25 may comprise rings of elongate or rectangular form fixed, as by a tape connected by stitches, to the opposite ends of the edges 18, 19. The bag assembly 14 may further include a closure such as a zipper 28 in one of the panels 16, 17 for closing an opening into the interior compartment 21.

Figure 5:
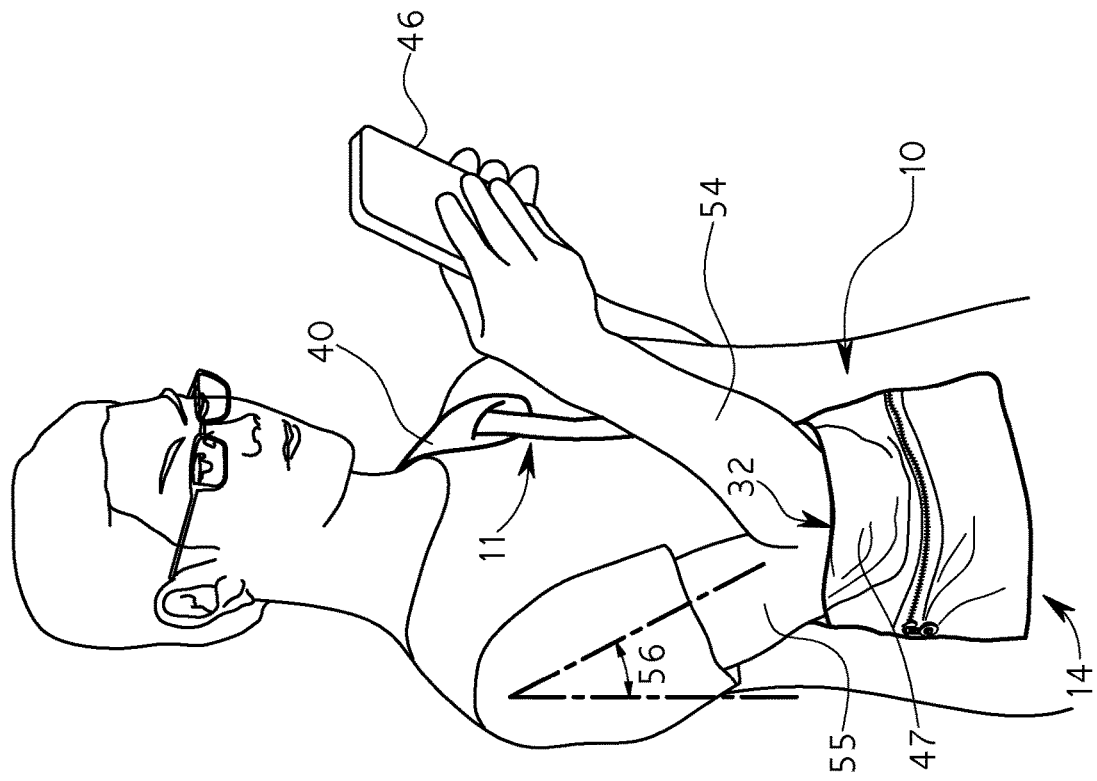
FIG. 5 is a perspective view of the unobtrusive elbow brace of the invention in use with the elbow-receiving sleeve in the open state.

The elbow-receiving sleeve 15 is formed of flexible sheet-like material and attached in the upper bag mouth 20 for movement, together with the mouth 20, between an open state for bracing the wearer's elbow (shown in FIGS. 2 and 5) and a closed state (shown in FIGS. 3 and 4) where the upper bag mouth 20 is in a closed state, as lying against the abdomen of the wearer, and the elbow-receiving sleeve 15 is largely hidden from view. The elbow-receiving sleeve 15 tapers to narrow from an outer end 32 received between the first and second panels 16, 17 adjacent the uppermost edges 18, 19, to an inner end 33. In the open state the elbow-receiving sleeve 15 has with a generally frustoconical form, with an included cone angle a of preferably between 75° and 105°, and most preferably of around 90°. In the closed state, the elbow-receiving sleeve 15 is flattened such that opposing halves 29, 30, fixed to respective ones of the panels 16, 17, come together.

Generally, as with flexible bag assembly 14, any flexible sheet-like material is suitable for forming the elbow-receiving sleeve 15, including polymer sheets, woven and knitted textiles, leather, mesh/netting etc, but it is preferred that the flexible sheet-like material provide some resilience. A preferred material is an elastomer, most preferably a foamed elastomer which provides resilience and cushioning.

For example, the elbow-receiving sleeve 15 may be made of 4 to 6 mm thick neoprene, which may be laminated with a textile piece on one or both sides (not shown). The frustoconical form and the resilience of this neoprene material, means that the elbow-receiving sleeve 15 is able expand circumferentially, from a rest state, when the elbow is inserted, thus firmly gripping a complementary surface of the elbow across the entirety of the elbow-receiving sleeve 15. Unobtrusive elbow braces 10 may be made with a range of different size elbow-receiving sleeves 15 to suit different users. The elbow-receiving sleeve 15 may be formed by a strip of this neoprene joined by a seam 31 to produce the frustoconical shape, with opposing halves 29, 30 of the elbow-receiving sleeve 15 fixed in the upper bag mouth 20 to respective ones of the panels 16, 17. The seam 31 may be disposed in a plane that bisects the elbow-receiving sleeve 15, with the opposing halves 29, 30 folding together along the seam 31 when they come together in the closed configuration.

Each half 29, 30 of the elbow-receiving sleeve 15 may be fixed generally at or adjacent both the outer end 32 and the inner end 33 to one of the first and second panels 16, 17, as by stitching about the perimeter of each of the halves 29, 30. This stitching may be done with each half slightly tensioned lengthwise, therefore providing some ability for the elbow-receiving sleeve 15 to expand circumferentially from its rest state.

The shoulder strap assembly 11 may include an elongate strap 37 to be positioned on the user's shoulder with a tension-locked buckle 38 connected to slide along the strap 37 to adjust the length of the shoulder strap assembly 11 to suit wearers of different sizes. One end 12 of the strap 37 is fixed to the tension-locked buckle 38 to form a first loop 39 passing through the aperture 26 in the fastening 24, then through the tension-locked buckle 38. The shoulder strap assembly 11 may include a pad 40 made of elastomer and movable along the length of the strap 37 to distribute the weight across the user's shoulder contacting the pad 40.

The shoulder strap assembly 11 may further include a D-shaped eye 41 fixed at an intermediate position along the strap 37, and a hook 43 fixed at an opposite end of the strap 37. The hook 43 is sized to receive the eye 41 and is closed by a resiliently mounted gate 51. From the end connected to the hook 43, the strap 37 passes through the aperture 27 to form a second loop 44 when the hook and eye 41, 43 are connected to define a shortened configuration. The hook 43 cannot pass through the aperture 27, so when the hook 43 is released from the eye 41, this defines a lengthened configuration. In this manner, by simply connecting and disconnecting the hook 43 and eye 41, the strap assembly is quickly toggled between shortened and lengthened configurations.

Figure 4:
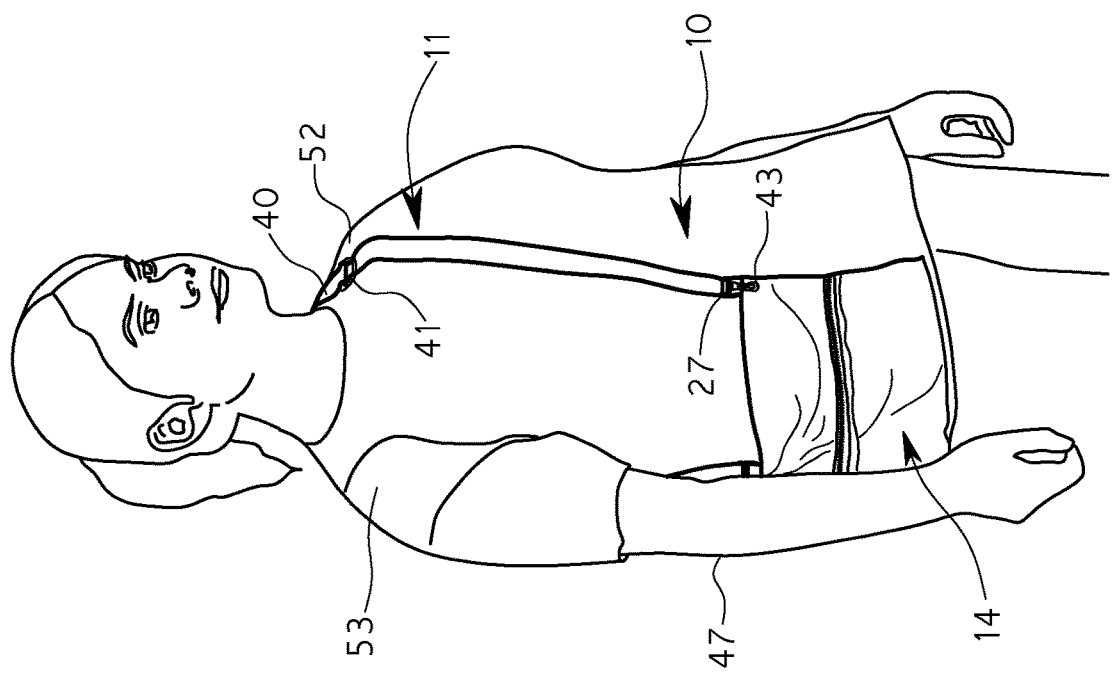
FIG. 4 is a perspective view of the unobtrusive elbow brace of the invention with the elbow-receiving sleeve in the closed state.

As shown in FIG. 4, with the shoulder strap assembly 11 in the lengthened configuration, the unobtrusive elbow brace 10 is worn like a shoulder bag, with the shoulder strap assembly 11 extending over one shoulder 52, and diagonally across the back and front of the torso, such that the flexible bag assembly 14 hangs against the side of the torso, below the other shoulder 53. The weight hanging below the upper bag mouth 20 tends to bring and/or hold the upper edges 18, 19 of the panels 16, 17 and the opposing halves 29, 30 of the elbow-receiving sleeve 15 together, so the elbow-receiving sleeve 15 is largely hidden from view. This lengthened configuration allows the unobtrusive elbow brace 10 to be comfortably worn and removed, while the zipper 28 is conveniently positioned for ready access to the compartment 21, as to retrieve a portable electronic device 46, and the hook 43 is conveniently positioned at the front.

When it is desired to use the portable electronic device 46, the hook 43 is engaged with the eye 41 to shorten the strap assembly 11. The diagonal alignment of the strap assembly 11 is maintained, so shortening it has the effect of raising the flexible bag assembly 14 and elbow-receiving sleeve 15. The upper bag mouth 20 and elbow-receiving sleeve 15 are opened by separating the panels 16, 17 and, with the wearer's elbow bent at around 90°, the wearer inserts his elbow 47 into the elbow-receiving sleeve 15 such that both his forearm 54 and upper arm 55 extend from the outer end 32 while the device hangs against the side of the abdomen. In this position the upper arm 55 may have an angle of flexion 56 of about 25°. With the strap length correctly adjusted, in this position, the unobtrusive elbow brace 10 provides support for the weight of the forearm 54, while the resilience of the elbow-receiving sleeve 15 provides progressive resistance to the extension of the forearm 54, thus tending to maintain the elbow bent at around 90°. The elbow-receiving sleeve 15 provides a sufficiently large surface area that the low contact pressure between the elbow and the sleeve 15 ensures comfort.

When the portable electronic device 46 is held in the hand of the arm supported in this way, with the neck upright, the device 46 may be 100-200 mm below the horizontal plane in which the wearer's eyes are positioned, so the device 46 can be readily seen without the need to tilt the head forward whether sitting, standing or walking. The unobtrusive elbow brace 10 thus encourages an upright posture in which neck strain, associated with a head-forward posture, is avoided. The resultant more upright orientation of the forearm 54, advantageously also reduces wrist strain.

Aspects of the present invention have been described by way of example only and it should be appreciated that modifications and additions may be made thereto without departing from the scope thereof.

The invention claimed is:

1. An unobtrusive elbow brace comprising:
a length-adjustable shoulder strap assembly having longitudinally opposing ends;
a flexible bag assembly comprising: opposite first and second panels of flexible sheet-like material that are mutually connected to define an interior compartment, upper edges of the first and second panels being mutually connected at opposite ends to form an upper bag mouth therebetween, a fastening at each of the opposite ends, the fastenings connecting respective ones of the opposing ends of the length-adjustable strap assembly;
an elbow-receiving sleeve formed of flexible sheet-like material and attached in the upper bag mouth for movement between open and closed states, the elbow-receiving sleeve tapering to narrow from an outer end proximate the upper edges, to an inner end, in the open state the elbow-receiving sleeve having with a generally frustoconical form, with an included cone angle between 75° and 105°, wherein, in use, the elbow-receiving sleeve receives a wearer's bent elbow such that both forearm and upper arm extend from the outer end, and in the closed state the elbow-receiving sleeve is flattened such that opposing halves of the elbow-receiving sleeve come together.

2. The unobtrusive elbow brace of claim 1, wherein the frustoconical form has a central axis, and the fastenings are disposed along a transverse axis substantially equidistant either side of the central axis.

3. The unobtrusive elbow brace of claim 1, wherein the flexible sheet-like material of the elbow-receiving sleeve comprises an elastomer.

4. The unobtrusive elbow brace of claim 3, wherein the elastomer comprises a foamed elastomer sheet.

5. The unobtrusive elbow brace of claim 1, wherein the flexible sheet-like material of the first and second panels comprises a textile.

6. The unobtrusive elbow brace of claim 1, wherein each half of the elbow-receiving sleeve is fixed generally at or adjacent both the inner and outer ends to one of the first and second panels, as by stitching or adhesive.

7. The unobtrusive elbow brace of claim 1, wherein the halves of the elbow-receiving sleeve are joined by at least one seam.

8. The unobtrusive elbow brace of claim 7, wherein the elbow-receiving sleeve folds along the at least one seam when the elbow-receiving sleeve is flattened.

9. The unobtrusive elbow brace of claim 1, wherein the flexible bag assembly further comprises a closure for closing an access opening in one of the first and second panels for accessing the interior compartment.

10. The unobtrusive elbow brace of claim 1, wherein the fastenings each include an aperture, the shoulder strap assembly comprises an elongate strap, a tension-locked buckle connected to slide along the strap and with one end of the strap fixed thereto to form a first loop passing through the aperture in one of the fastenings, and a first coupler fixed at an intermediate position along the strap, an opposite end of the strap fixed to a second coupler complementary to the first coupler and passing through the aperture of the other of the fastenings to form a second loop when the first and second couplers are connected.

11. The unobtrusive elbow brace of claim 10, wherein the first coupler is an eye and the second coupler is a hook with a mouth sized to receive the eye and closed by a resiliently mounted gate.

12. The unobtrusive elbow brace of claim 11, wherein the second coupler is unable to pass through the aperture of the other of the fastenings.

* * * * *